(12) United States Patent
Schneider et al.

(10) Patent No.: US 6,268,516 B1
(45) Date of Patent: Jul. 31, 2001

(54) CATIONIC AMPHIPHILIC LIPIDS FOR LIPOSOMAL GENE TRANSFER

(75) Inventors: Manfred Schneider; Oliver Keil, both of Wuppertal; Regina Reszka, Schwanebeck; Detlef Groth, Ferch, all of (DE)

(73) Assignee: Max-Delbruck-Centrum fur Molekulare Medizin (DE)

( * ) Notice: Subject to any disclaimer, the term of this patent is extended or adjusted under 35 U.S.C. 154(b) by 0 days.

(21) Appl. No.: 09/230,842
(22) PCT Filed: Aug. 1, 1997
(86) PCT No.: PCT/DE97/01669
  § 371 Date: Mar. 30, 1999
  § 102(e) Date: Mar. 30, 1999
(87) PCT Pub. No.: WO98/05678
  PCT Pub. Date: Feb. 12, 1998

(30) Foreign Application Priority Data

Aug. 2, 1996 (DE) .............................................. 196 31 189

(51) Int. Cl.[7] .................................................. C07C 229/00
(52) U.S. Cl. ............................................ 554/105; 554/107
(58) Field of Search ...................................... 554/105, 107

(56) References Cited

FOREIGN PATENT DOCUMENTS

95/04030 * 2/1995 (WO) .

* cited by examiner

Primary Examiner—Barbara P. Badio
(74) Attorney, Agent, or Firm—Norris, McLaughlin & Marcus

(57) ABSTRACT

This invention relates to the synthesis of novel cationic, amphiphilic lipids and their application as gene transfer vehicles in vitro and in vivo. For this a series of different lipids (diglycerides, steroids) were synthesized by modification with variable cationic molecules (amino acids, biogenic amines). Compounds of this kind are, due to their capability of producing complexes with polynucleotides (DNA, RNA, Antisense oligonucleotides, ribozymes etc) suitable as vectors for gene transfer (transfection).

3 Claims, 6 Drawing Sheets

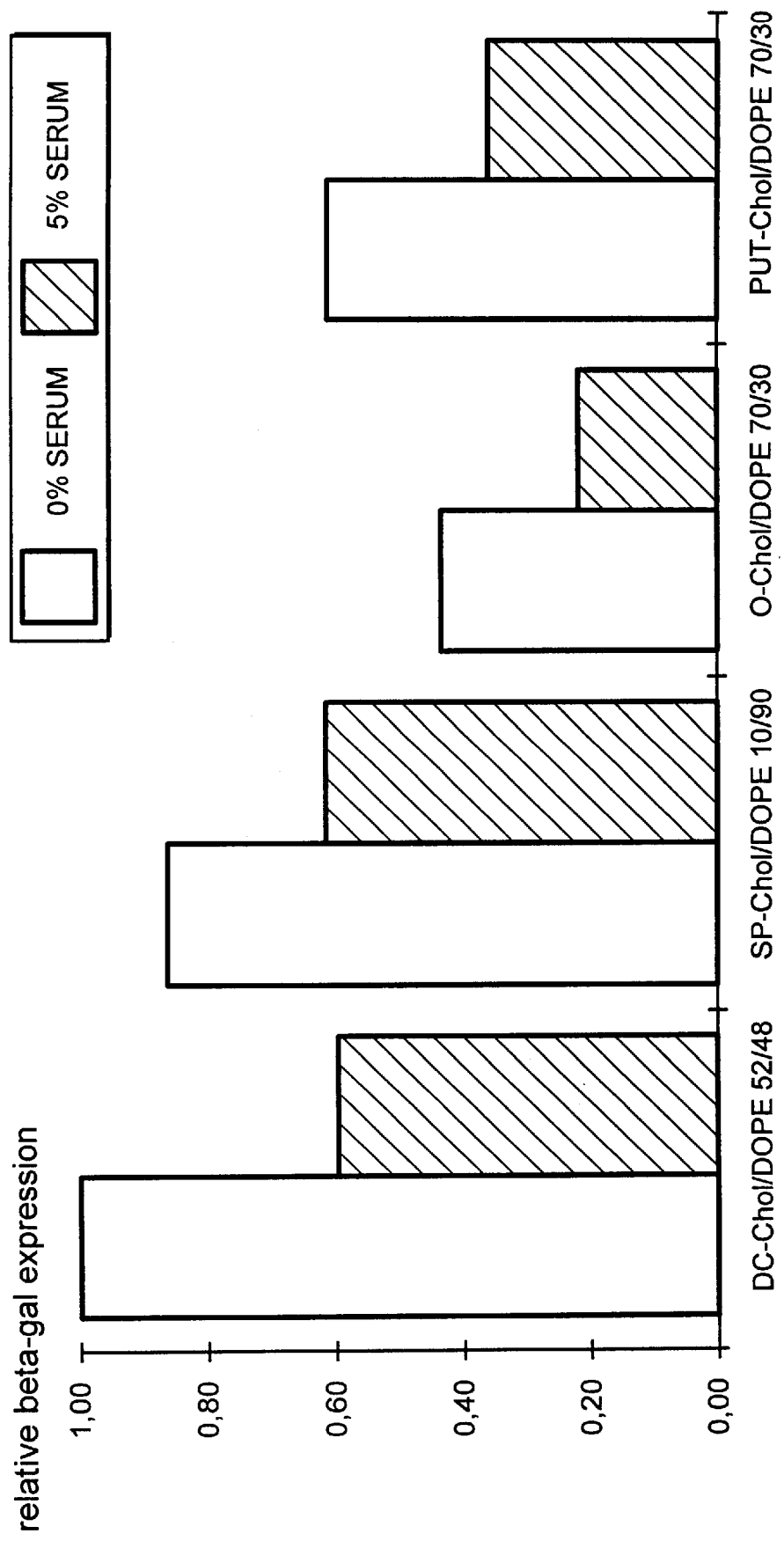
F I G. 1

CATIONIC AMPHIPHILIC LIPIDS FOR LIPOSOMAL GENE TRANSFER

This application is a 371 of PCT/DE97/01669 filed Aug. 1, 1997.

The invention relates to cationic lipids of the general formula I,

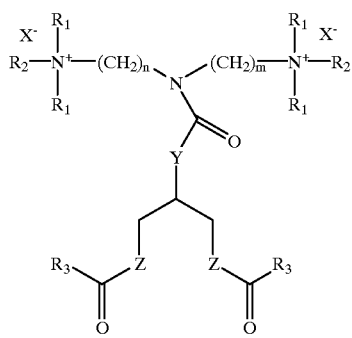

I whereby n can be =2,3,4,6,8 and m can be =3,6,8 and where $R_1$ represents H, $CH_3$ $CH_2CH_2OH$; $R_2$ represents H, $CH_3$, $CH_2CH_2OH$, $(CH_2)_3N^+(R_1)_3$, $R_3$ represents a straight chain, saturated or unsaturated aliphatic group $C_7$–$C_{21}$, Z represents $CH_2$, O, NH, Y represents $CH_2$, O, NH and X represents Cl, Br, I, $CH_3COO$, $CF_3COO$;

cationic lipids of the general formula Ia,

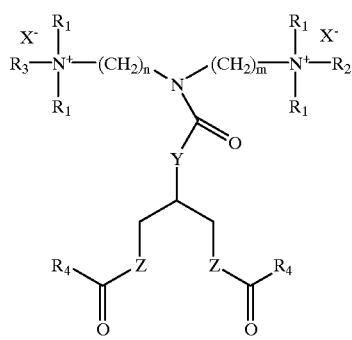

wherein n and m can be n=2, 3, 4, 6, or 8 and m=2, 3, 6, or 8 and $R_1$=H, $CH_3$, or $CH_2CH_2OH$; $R_2$=H, $CH_3$, $CH_2CH_2OH$, or $(CH_2)_3N^+(R_1)_3$, $R_3$=H, $CH_3$, $CH_2CH_2OH$, or $(CH_2)_3N^+(R_1)_3$, $R_4$ represents a straight chain saturated or unsaturated aliphatic group $C_7$–$C_{21}$, Z=$CH_2$, O, or NH, Y=$CH_2$, O or NH and X=Cl, Br, I, $CH_3COO$, or $CF_3COO$;

cationic lipids of the formula II,

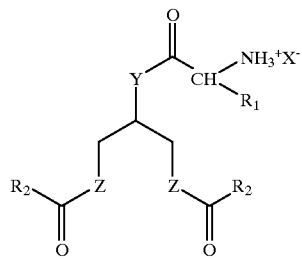

II whereby $R_1$ represents an aliphatic, aromatic or heteroaliphatic α-carbon atom substituent of the α-amino acids glycine, alanine, valine, leucine, isoleucine, phenylalanine, trosine proline, hydroxyproline, serine, threonine, cysteine, cystine, methionine, tryptophane arginine, lysine, ornithine, histidine, and $R_2$ represents a straight chain saturated or unsaturated aliphatic group $C_7$–$C_{21}$, X=Cl, Br, I, $CH_3COO$, $CF_3COO$, Y=$CH_2$, O, NH and Z=$CH_2$, O, NH;

cationic lipids of the general formula III,

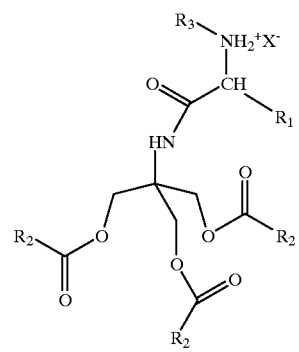

III whereby $R_1$ represents H, $CH_3$, $(CH_2)_3NH_2^+X^-(CH_2)_3NH_3^+X^-$, $R_3$=H, $(CH_2)_3NH_3^+X^-$, and $R_2$ a straight chain saturated or unsaturated aliphatic group $C_7$–$C_{21}$ and X=Cl, Br, I, $CH_3COO$, $CF_3COO$;

cationic lipids of the general formula IV,

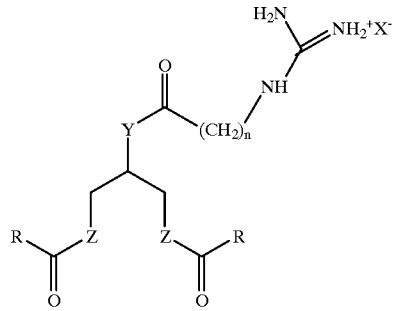

IV whereby n can be 1–4 and R represents a straight chain, saturated or unsaturated aliphatic group $C_7$–$C_{21}$, Y represents $CH_2$, O, NH, Z represents $CH_2$, O, NH and X represents Cl, Br, I, $CH_3COO$, $CF_3COO$;

cationic lipids of the general formula V,

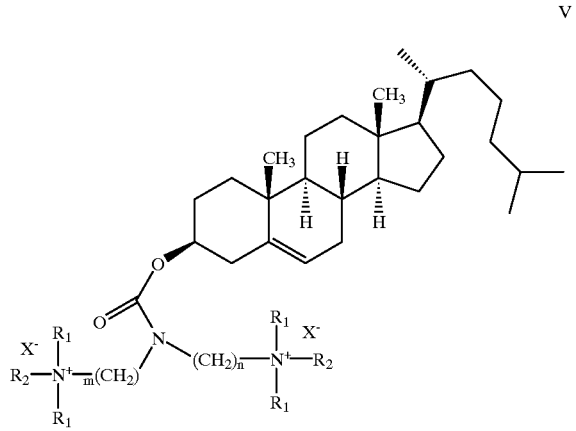

whereby n can be =2,3,4,6,8 and m can be =2,3,6,8 and $R_1$ represents H, $CH_3$, $CH_2CH_2OH$; $R_2$ represents H, $CH_3$, $CH_2CH_2OH$, $(CH_2)_3N^+(R_1)_3$ and X represents Cl, Br, I, $CH_3COO$, $CF_3COO$;

cationic lipids of the general formula VI,

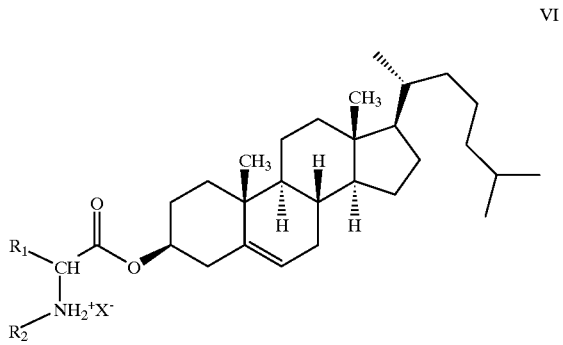

whereby $R_1$ represents H, $CH_3$, $(CH_2)_3NH_2^+X^-(CH_2)_3NH_3^+$ $X^-$, $(CH_2)_3NH_3^+X^-$, $R_2$ represents H, $(CH_2)_3NH_3^+X^-$ and X represents Cl, Br, I, $CH_3COO$, $CF_3COO$;

cationic lipids of the general formula VII,

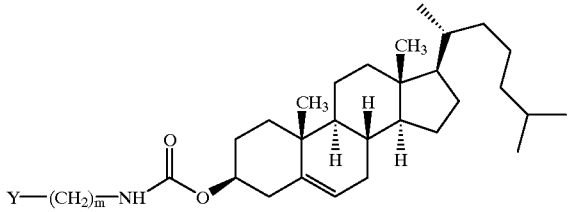

whereby m can be =2–6 and Y represents a group $N(R)_3^+X^-$ in which R represents H, $CH_3$, $(CH_2)_2OH$ or a group $NH—C(NH_2^+X^-)NH_2$ in which X represents Cl, Br, I, $CH_3COO$, $CF_3\,COO$;

cationic lipids of the general formula VIII,

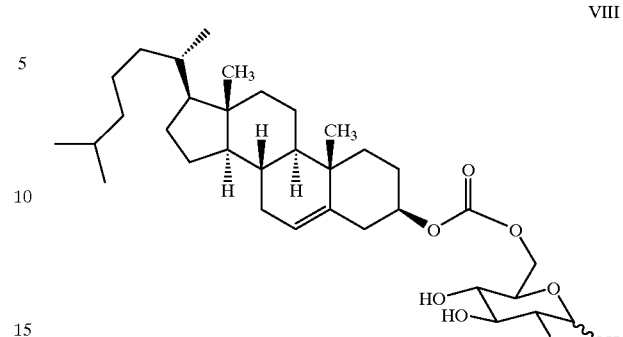

whereby Y represents a group $N(R)_3^+X^-$ in which R represents H, $CH_3$, $(CH_2)_2OH$ or a group $NH—C(NH_2^+X^-)NH_2$ in which X represents Cl, Br, I, $CH_3COO$, $CF_3COO$;

cationic lipids of the general formulas IX und X,

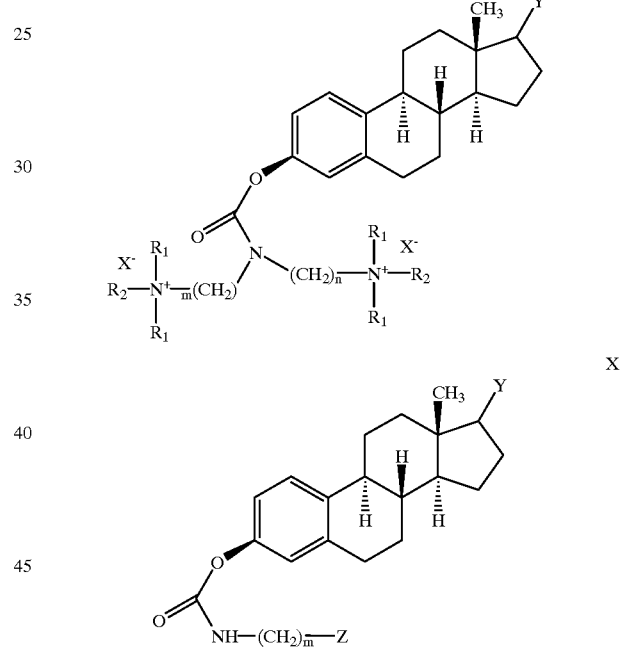

whereby n can be =3,4,6,8 and m can be =2,3,6,8 and $R_1$ represents H, $CH_3$, $CH_2CH_2OH$, $R_2$ represents H, $CH_3$, $CH_2CH_2OH$, $(CH_2)_3N^+(R_1)_3$, R represents H, $CH_3$, $(CH_2)_2OH$, Y represents a carbonyl group (=O (estrone)) or a hydroxy group OH (estradiol), Z represents a group $N(R)_3^+X^-$ in which R represents H, $CH_3$, $(CH_2)_2OH$ or a group $NH—C(NH_2^+X^-)NH_2$ and whereby X represents Cl, Br, I, $CH_3COO$, $CF_3COO$.

Cationic lipids of the general formulas I–X are suitable reagents for liposomal gene transfer (transfection). Applications for such transfection reagents are in medicine and gene technology. The delivery of genetic material into eukaryotic cells is a fundamental method for studies of biological functions and of increasing importance for the gene therapeutic treatment of various diseases whereby tumours have to be mentioned foremost.

One differentiates thereby between biological, physical and physico-chemical methods for the transfer of DNA, RNA and proteins into target cells [Wagner J, Madry, H., Reszka, R (1995). In vivo gene transfer: focus on the kidney. Nephrol. Dial. Transplant 10:1801–1807 Zhu J, Zhang L, Hanisch U-K, Felgner P L,. Reszka R (1996). In vivo gene therapy of experimental brain tumors by continuous administration of DNA-liposome complexes. Gene Therapy 3: 472–476, Kiehntopf, M., Brach MA & Hermann F (1995). Gentherapie in der Onkologie: Perspektiven, Chancen und Risiken. Onkologie 18 (Sonderheft): 16–26]. Physical methods like electroporation and micro injection are only suitable for ex vivo and in vitro transfer. The so-called "Jet"-injection method can be used in addition also for the in vivo gene transfer (liver, skin). Physico-chemical methods like the calcium phosphate precipitation technique (cpp) or DEAE-dextrane transfection are limited to in vitro and ex vivo applications.

Retroviral gene transfer using virus producing cells, as presently being tested in a series of clinical trials (phase III) is characterised by a relatively long lasting, however, relatively low gene expression in the dividing cells. Problematic in the retroviral gene transfer are mainly the development of a specific immuno answer against the implanted, virus producing helper cells, the possible generation of replication competent viruses and the danger of activating cellular oncogenes or, possibly, the deactivation of suppressor genes as a result of the accidental localisation of gene insertion. The comprehensive, required cell biological and medicinal preparational work and the expensive safety measures lead to high expected costs in the clinical applications of retro viral gene transfer.

Vectors based on adenoviruses are also attractive gene transfer vehicles. They acchieve high transfection rates also in non dividing tissue. However, since the DNA here is not integrated into the genome, the duration of the expression of the foreign gene is limited and the repeated application in vivo is hampered by the strong and specific immuno answer of the host organism during repeated applications.

In contrast, the liposomal gene transfer has gained in recent years in importance also for applications in vivo. The gene constructs can either be encapsulated in liposomes or are associated to their membranes. Liposomal preparations are characterised by facile handling, low immuno reaction and thus the possibility for repeated applications leading to reduced risks both for applicant and "receiver" (patient). The application of immuno liposomes as transport vehicles for genetic material is still at a very early stage.

Another also quite interesting approach constitutes the use of fusogenic liposomes which carry in their interior a complex formed by DNA and nuclear protein (HMG I) [Kaneda, Iwai, K., Uchida, T(1989). Increased expression of DNA cointroduced with nuclear protein in adult rat liver Science 243, 375–378,Kaneda Y, Kato, K., Nakanishi, M., Uchida, T.(1996) Introduction of plasmid DNA and nuclear protein into cells by using erythrocyte ghosts, liposomes, and Sendai virus. Methods-Enzymol. 221:317–327].

For a number of years now cationic liposomes are applied successfully for the transfer of DNA (Felgner P L, Gadek T R, Holm M et al. (1987). Lipofection: a highly efficient, lipid-mediated DNA transfection procedure. Proc Natl Acad Sci USA 84:7413–7417, Felgner J R Kumar R, Sridhar C N et al. (1994). Enhanced gene delivery and mechanism studies with a novel series of cationic lipid formulations. J Biol Chem 269:2550–2561), antisense-oligomers, proteins and ribozymes. By electrostatic interaction DNA is associated with the membrane of the liposomes and transfected into the cell by a mechanism which up to now is only incompletely understood. The transfection rate in vitro is thereby dependent on the specific cell line, however comparable with the efficacy of retroviral gene transfer. Presently the firs cationic liposome/DNA/complexes [DMRIE/DOPE und DOTMA/DOPE (Lipofectin, Gibco BRL USA) sowie DC-Chol/DOPE] are in a clinical phase I/II trial (Gao, X., Huang, L. (1995 Cationic liposome-mediated gene transfer. Gene Therapy 2:710–722).

Cationic, amphiphilic molecules, consisting of a lipid moiety (steroidal or diglyceride skeleton) and a positive head group (ammonium ion) are capable to form liposomes, either spontaneously or after addition of a helper lipid like dioleoylphosphatidylethanolamine (DOPE).

Via electrostatic interactions DNA is associated with the liposome membranes and delivered into the cell by a mechanism which up to now is only incompletely understood.

In order to achieve a highly efficient gene transfer both in vitro and in vivo the cationic lipids employed for the generation of liposomes should fulfill the following criteria:
1. They should be non-toxic, fully biodegradable and should not cause any immuno reaction
2. They should form complexes with DNA with high efficacy, should protect DNA against degradation and should show high transfection rates
3. They should transfect cells receptor specific
4. They should be accessible by synthesis easily and in larger quantities Both the methods for synthesis of cationic lipids and the molecules themselves as described in the literature so far display a number of disadvantages. Thus the synthesis of the commercial transfection reagents such as DOTMA (Lipofektin), DOGS und DOSPA requires numerous reaction steps several of which display only very low yields. In addition they require for their purification tedious colum chromatographic procedures.

In many compounds such as DOTMA, DMRIE und DOSPA the cationic head groups are connected with long chain fatty alcohols via ether linkages which cause a reduced biodegradability and thus high toxicity of these molecules. Basis for this invention was the task to find novel cationic lipids which would—in comparison with known materials—display higher gene transfer rates and at the same time lower toxicities. Further basis for this invention was the task to develop procedures by which the syntheses of these cationic lipids can be achieved in a few reaction steps and with high yields. These tasks were solved in accordance with the claims I–IX. With the novel cationic lipids having the general formulas I–XI compounds are made available which fulfill the criteria summarized above. Thus in FIGS. 2–6 it is demonstrated with several tumour cell lines that the liposomes prepared from the lipids SP-Chol, O-Chol, Put-Chol and DOSGA together with the helper lipid dioleoylphosphatidylethanolamine (DOPE) (in the described molar ratios) are transfecting in the absence of serum with higher efficacy as compared to DC-Chol/DOPE vesicles.

Using the rat colon carcinoma cell line CC531 (FIG. 3) SP-Chol and O-Chol/DOPE are transfecting with significantly higher efficacy in presence of 5% serum as compared to DC-Chol/DOPE.

Particularly surprising are the high transfection rates shown in FIGS. 5 and 6 which were found with the use of DOSGA/DOPE liposomes in presence of 5% serum with human and rat glioblastoma cell lines (N 64, F 98). SP-Chol/DOPE liposomes have also been proven to be highly suited in serum containing media for the transfection of human breast tumour cell lines (MaTu) (FIG. 1).

Classification of the lipids:

| lipid | class of compound |
|---|---|
| DC-Chol | I β[N-(N',N'-dimethylaminoethane)-carbamoyl]cholesterol |
| Sp-Chol | V example 4 |
| Put-Chol | VII example 4 |
| O-Chol | VI example 5 |
| DOSGA | IV example 3 |

The synthesis of the invented compounds is carried out according to the added Schemes.

Scheme I describes the procedure for the synthesis of novel cationic lipids with 1,3-diglyceride backbone to which the cationic head group is attached via a carboxylate spacer.

Scheme II describes the procedure for the syntheses of 1,3-diglyceride modified amino acids.

Scheme III describes the procedure for the syntheses of 1,3-diglyceride modified guanidinium derivatives.

Scheme IV describes the procedure for the syntheses of novel cholesterol derivatives with biogenic amines as cationic head groups.

Scheme V describes the procedure for the syntheses of amino acid modified cholesterol derivatives.

Scheme VI describes the procedure for the syntheses of glucosamine modified cholesterol derivatives.

Scheme VII describes the procedure for the syntheses of cationic modified estradiol derivatives.

Scheme VIII describes the procedure for the syntheses of cationic modified estrone derivatives.

In summary, it can be stated that it is now possible by using the described procedures to synthesize under cost effective conditions and by employing low cost chemicals transfection reagents which display unexpectedly high transfection rates and a good biodegradability.

BRIEF DESCRIPTION OF THE DRAWINGS

FIG. 1 is a graph showing relative beta-gal expression for transfection of MaTu-cells;

Figure 2:
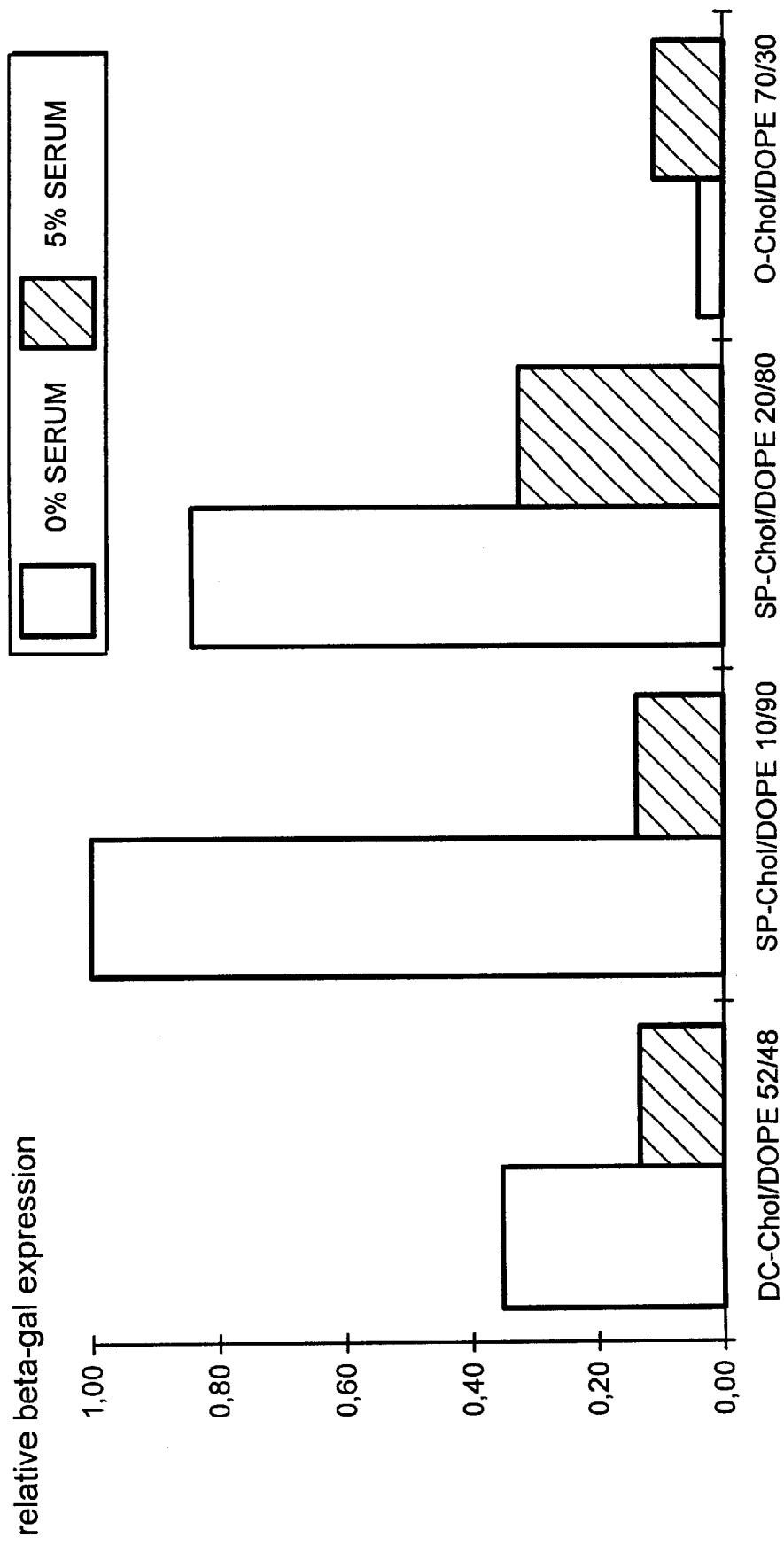
FIG. 2 is a graph showing relative beta-gal expression for transfection of F98-cells.
Figure 3:
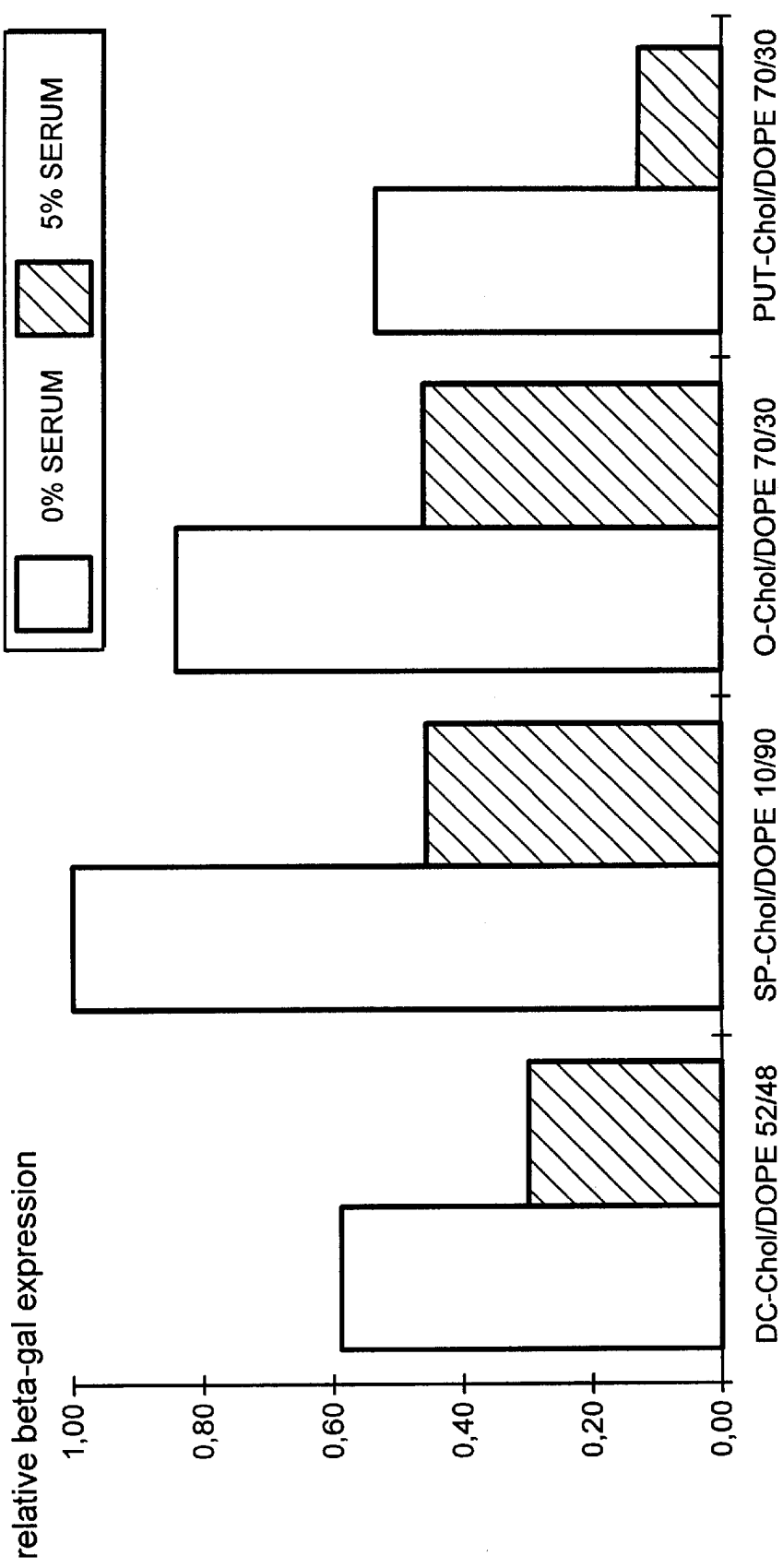
FIG. 3 is a graph showing relative beta-gal expression for transfection of CC531-cells
Figure 4:
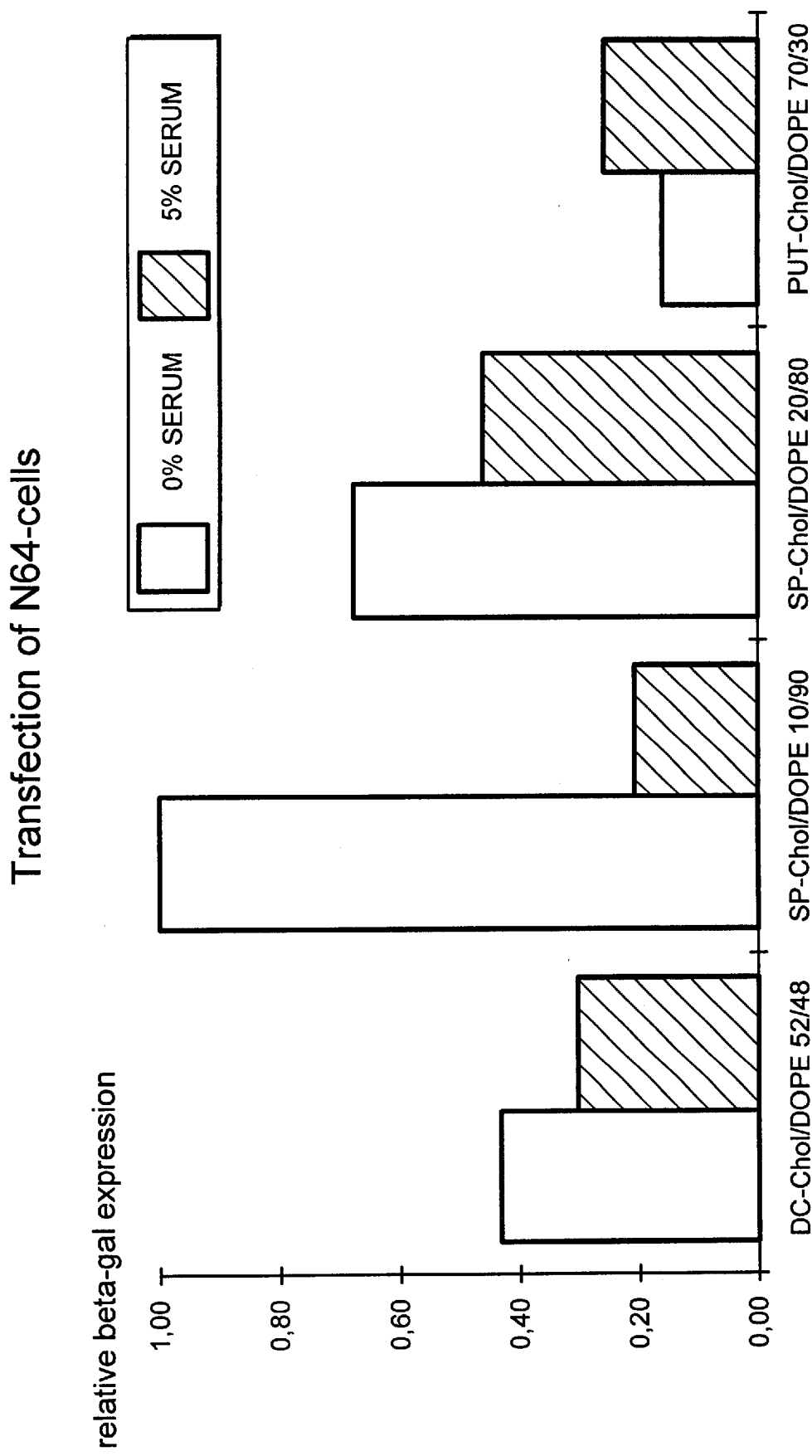
FIG. 4 is a graph showing relative beta-gal expression for transfection of N64-cells.
Figure 5:
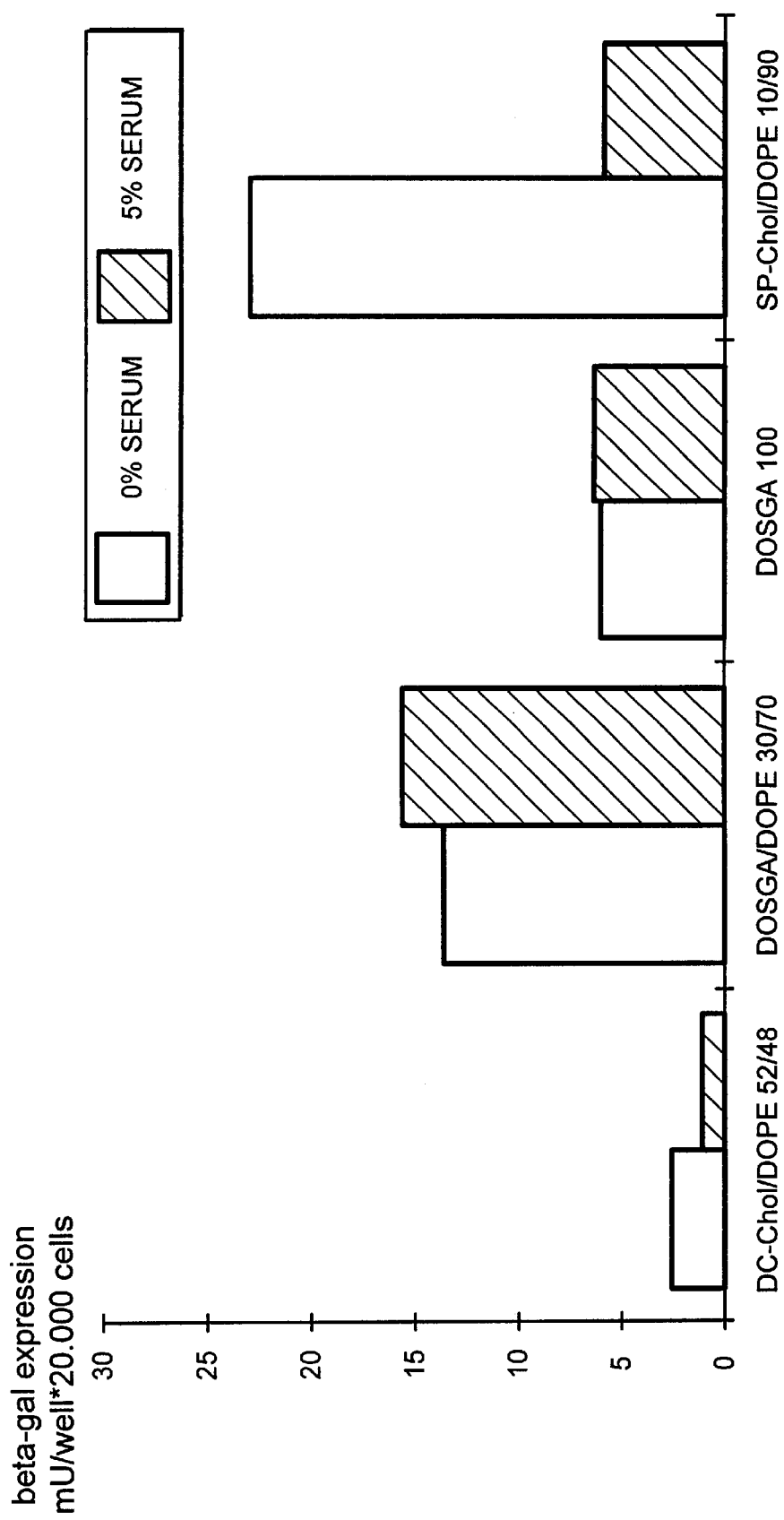
FIG. 5 is a graph showing beta-gal expression mU/well*20.000 cells for transfection of F98-cells.
Figure 6:
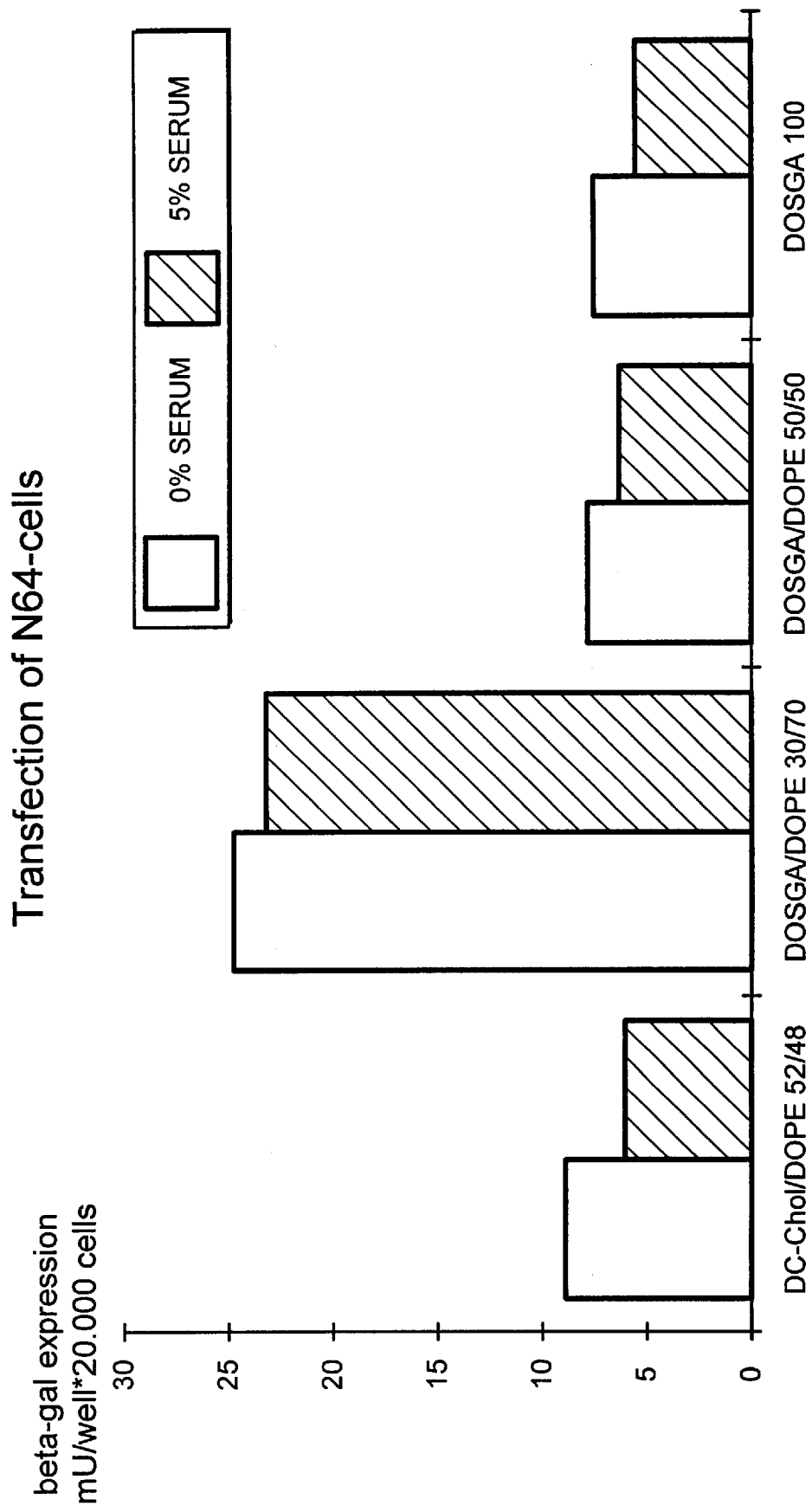
FIG. 6 is a graph showing beta-gal expression mU/well*20.000 cells for transfection of N64-cells.

The invention is further illustrated below by a number of examples Examples

EXAMPLE 1

Synthesis of 2-($N^5$-carbamoyl-($N^1,N^{10},N^{14}$-ammoniumtetraazadecane))-1,3-dioleoyloxy-propane-tris-trifluoroacetate I To 247 μl (1 mmol) of 1,3-dibenzyloxy-2-propanol 7 ml of a 20% solution of phosgene in toluene was added and the mixture was stirred for 48 h at room temperature. After this period the flask was flushed with argon in order to remove the excess phosgene and the remaining solution was added dropwise to a solution of 302 mg (0.6 mmol) of $N^1N^{10}N^{14}$-tris-BOC-spermine and 300 μl of triethylamine in 5 ml of dichloromethane and the mixture was stirred for 4 h at room temperature. Subsequent purification by column chromatography (silica 60) yielded 375 mg (47%) of 2-(N5-carbamoyl-($N^1,N^{10},N^{14}$-tris-BOC-tetraazadecane))-1,3-dibenzyloxy-propanol as a viscous oil.

670 mg (0.84 mmol) of 2-($N^5$-carbamoyl-($N^1,N^{10},N^{14}$-tris-BOC-tetraazadecane))-1,3-dibenzyloxy-propanol was dissolved in 25 ml of ethanol and was hydrogenated for 24 h in the presence of 150 mg Pd/C (5%). After removal of the catalyst 520 mg (100%) of 2-($N^5$-carbamoyl-($N^1,N^{10},N^{14}$-tris-BOC-tetraazadecan))-1,3-propantriol was obtained as a viscous oil.

452 mg (1.6 mmol) of oleic acid, 334 mg (1.62 mmol) of DCC and 20 mg of DMAP were added to a solution of 472 mg (0.76 mmol) of 2-($N^5$-carbamoyl-($N^1,N^{10},N^{14}$-tris-BOC-tetraazadecane))-1,3-propantriol in 30 ml of dichloromethane, and the mixture was stirred at room temperature for 24 h. Subsequent purification by column chromatography (silica 60 afforded 457 mg (52%) of 2-($N^5$-carbamoyl-($N^1N^{10}N^{14}$-tris-BOC-tetraazadecane))-1,3-dioleoyloxy-propane as a viscous oil.

200 mg (0.17 mmol) of 2-($N^5$-carbamoyl-($N^1,N^{10},N^{14}$-tris-BOC-tetraazadecane))1,3-dioleoyloxy-propane was treated with 3 ml of TFA/$CH_2Cl_2$ (1:1) and the mixture was stirred for 30 min at room temperature. Dilution of the mixture with 10 ml of dioxane and removal of the solvents in vacuo yielded 202 mg (99%) of 2-($N^5$-carbamoyl-($N^1,N^{10},N^{14}$-ammoniumtetraazadecane))-1,3-dioleoyloxypropane-tris-trifluoroacetate I as a colorless, viscous oil.

EXAMPLE 2

Synthesis of 2-L-alanyl-(1,3-dioleoyloxy) propylamide-trifluoroacetate II 4 mmol (756 mg) of Boc-L-alanine (M=189.21) and 4.3 mmol (436 mg=600 μl) of triethylamine (M=101.19, d=0.726) were dissolved in 10 ml of anhydrous tetrahydrofuran and the resulting solution was cooled to −10° C. in acetone/liquid nitrogene. After that 4 mmol (320 μl) of methyl chloroformate (M=94.50, d=1.228) was added, and the mixture was stirred for 30 min at 0° C. After addition of 5 mmol (456 mg) of 2-amino-1,3-propanediol (M=91.11) the mixture was stirred for an additional hour at ambient temperature. The solvent was then removed in vacuo, and the residue was dissolved in 50 ml of ethylacetate. The organic layer was washed with 5 ml of saturated aqueous $NaHCO_3$ soln. followed by 10 ml of brine and was dried over $Na_2SO_4$. After concentration in vacuo and removal of residual traces of solvents under high vacuum 332 mg (32%) of 2-BOC-L-alanyl-(1,3-dihydroxy)propylamide was obtained as a colorless liquid.

2.28 mmol (598 mg) of 2-BOC-L-alanyl-(1,3-dihydroxy) propylamide, 5.70 mmol (1.610 g) of oleic acid (M=282.47), 5.70 mmol (1.176 g) of dicyclohexylcarbodiimide (M=206.33) and 0.23 mmol (28 mg) of dimethylaminopyridine (M=122.17) were dissolved in 40 ml of abs. $CH_2Cl_2$ and stirred for 12 h at ambient temperature. Subsequent purification by column chromatography (silica 60) yielded 1.450 g (80%) of 2-BOC-L-alanyl-(1,3-dioleoyloxy) propylamide.

0.89 mmol (702 mg) of 2-BOC-L-alanyl-(1,3-dioleoyloxy)propylamide was treated with 6 ml of TFA/$CH_2Cl_2$ (1:1) for 30 min at room temperature. After dilution of the mixture with 10 ml of dioxane and removal of the solvents in vacuo 712 mg (99%) of 2-L-alanyl-(1,3-dioleoyloxy)propylamide-trifluoroacetate II were obtained.

EXAMPLE 3

Synthesis of 2-(amidino-β-alanyl)-1,3-dioleoyloxypropylamide-hydrochloride III

The reaction of 1.892 g (10 mmol) of N-BOC-β-alanine in analogy to example 2 afforded 2-BOC-β-alanyl-1,3-dioleoyloxypropylamide (15% overall yield). 500 mg (0.64 mmol) of 2-BOC-β-alanyl-1,3-dioleoyloxypropylamide was treated with 3 ml of TFA/CH$_2$Cl$_2$ (1:1) for 30 min at room temperature. The mixture was diluted with 50 ml of dichlormethane and extracted twice with 5 ml of saturated aqueous NaHCO$_3$ soln. The organic layer was dried over sodium sulfate and the solvent removed in vacuo. The residue was redissolved in 20 ml of DMF and was stirred with 103 mg (0.7 mmol) of 1-H-pyrazol-1-carboxamidine-hydrochloride and 120 µl (0.7 mmol) of DIEA at room temperature overnight. Subsequent purification of the crude product by column chromatography (silica 60) yielded 480 mg (98%) of 2-(amidino-p-alanyl)-1,3-dioleoyloxypropylamide-hydrochloride m as a viscous oil.

EXAMPLE 4

Synthesis of 30-(N$^5$-carbamoyl-(N$^1$,N$^{10}$,N$^{14}$-ammoniumtetraazadecane))-cholesterol-tris-hydrochloride V 610 mg (1.2 mmol) of N$^1$,N$^{10}$,N$^{14}$-tris-BOC-spermine was dissolved in 10 ml of dichloromethane and 674 mg (1.5 mmol) of cholesteryl-chloroformate as well as 210 µl (1.5 mmol) of NEt$_3$ were added. The mixture was stirred for 4 h at ambient temperature and was subsequently purified by column chromatography yielding 570 mg (52%) of 3β-(N$^5$-carbamoyl-(N$^1$,N$^{10}$,N$^{14}$-tris-BOC-tetraazadecane))-cholesterol as a colorless foam. 275 mg (0.3 mmol) of 3β-(N$^5$-carbamoyl-(N$^1$,N$^{10}$,N$^{14}$-tris-BOC-tetraazadecane))-cholesterol was stirred with 6 ml of MeOH (10 mmol HCl) for 30 min at room temperature. After removal of the solvent under high vacuum 205 mg (94%) of 3p-(N$^5$-carbamoyl-(N$^1$,N$^{10}$,N$^{14}$-ammoniumtetraazadecane))-cholesterol-tris-hydrochloride V was obtained as a colorless solid. In a similiar manner 3β-(N-ammonium-N'-carbamoyl-1,4-diaminobutane)-cholesterol-hydrochloride VII (colorless solid) was synthesized starting from BOC-putrescine.

EXAMPLE 5

Synthesis of 3β-omithyl-cholesterol-dihydrochloride VI 997 mg (3 mmol) of di-BOC-ornithine was dissolved in 40 ml of dichloromethane. 1.16 g (3 mmol) of cholesterol, 640 mg (3.1 mmol) of DCC, and 50 mg of DMAP were added, and the mixture was stirred at room temperature for 24 h. The dicyclohexylurea precipitate was removed by filtration, the solvent removed in vacuo and the residual solid was recrystallized from 5 ml of hexane yielding 1.62 g (77%) of 3β-BOC-ornithyl-cholesterol as a colorless, crystalline solid. 190 mg (0.27 mmol) of 3β-di-BOC-ornithyl-cholesterol was treated with 6 ml of MeOH (10 mmol HCl) and was stirred at ambient temperature for 1 h. Subsequent removal of the solvent under high vacuum yielded 146 mg (94%) of 3β-ornithyl-cholesterol-dihydrochloride VI as a colorless solid.

EXAMPLE 6

Synthesis of 6-(3β-carboxycholesteroyl)-glucosamine-hydrochloride VIII 279 mg (1 mmol) of N-BOC-glucosamine was dissolved in 8 ml of pyridine. After addition of 449 mg (1 mmol) of cholesteryl chloroformate the mixture was stirred at room temperature for 24 h. Thereafter the pyridine was removed under high vacuum, the residual solid was dissolved in 50 ml of ether and extracted with 0.01 N HCl. The organic layer was concentrated in vacuo and the thus obtained residue was purified by column chromatography (silica 60) yielding 210 mg (30%) of 6-(3β-carboxycholesteroyl)-N-BOC-glucosamine as a colorless solid. 100 mg (0.15 mmol) of 6-(3β-carboxycholesteroyl)-N-BOC-glucosamine was treated with 3 ml of MeOH (5 mmol HCl) and the mixture was stirred at ambient temperature for 60 min. After removal of the solvents under high vacuum 95 mg (99%) of 6-(3β-carboxycholesteroyl)-glucosamine-hydrochloride VIII was obtained as a colorless. viscous oil.

EXAMPLE 7

Synthesis of 3-(N$^5$-carbamoyl-(N$^1$,N$^{10}$,N$^{14}$-ammoniumtetraazadecane))-estradiol-tris-hydrochloride IX 216 mg (0.8 mmol) of estrone was dissolved in 10 ml of dioxane. After addition of 241 µl (2 mmol) of diphosgene and 152 µl (1.2 mmol) of dimethylaniline the mixture was stirred as ambient temperature for 12 h. The mixture was then concentrated under high vacuum and the residual solid was taken up in 15 ml of dichloromethane. The thus obtained solution was added dropwise to a solution of 300 mg (0.6 mmol) of N$^1$,N$^{10}$,N$^{14}$-tris-BOC-spermine and 277 µl (2 mmol) of triethylamine in 5 ml of dichloromethane, and the mixture was stirred at room temperature for 4 h. Subsequent purification by column chromatography afforded 290 mg (61%) of 3-(N$^5$-carbamoyl-(N$^1$,N$^{10}$N$^{14}$-tris-BOC-tetraazadecane))-estrone as a viscous oil.

220 mg (0.28 mmol) of 3-(N$^5$-carbamoyl-(N$^1$,N$^{10}$,N$^{14}$-tris-BOC-tetraazadecane))-estrone was then dissolved in 5 ml of dioxane to which 37 mg (0.96 mmol) of sodium borohydride was added. After stirring for two hours at room temperature the pH of the mixture was adjusted to pH=6 with 1 N HCl and the solution was extracted three times with 50 ml of dichloromethane. The combined organic layers were dried over sodium sulfate and the solvent was removed on a rotary evaporator yielding 219 mg (96%) of 3-(N5-carbamoyl-(N$^1$,N$^{10}$,N$^{14}$-tris-BOC-tetraazadecane))-estradiol as a colorless foam.

In accordance with example 4 the thus obtained substance was treated with MeOH/HCl to give 3-(N$^5$-carbamoyl-(N$^1$, N$^{10}$,N$^{14}$-ammoniumtetraazadecane))-estradiol-tris-hydrochloride IX.

EXAMPLE 8

Synthesis of 3-(N,N-dimethylammoniumethylenediamine-N'-carbamoyl)-estrone-hydrochloride X 541 mg (2 mmol) of estrone was dissolved in 20 ml of dioxane. After addition of 603 µl (5 mmol) of diphosgene and 380 µl (3 mmol) of dimethylaniline the mixture was stirred as ambient temperature for 12 h. After that the solvent was removed under high vacuum and the residue was redissolved in 15 ml of dichloromethane. 800 µl (7.3 mmol) of N,N-dimethylaminoethylendiamine was added to the thus obtained solution and the mixture was stirred at room temperature for 4 h before being diluted with 100 ml of dichloromethane. The solution was extracted five times with 20 ml of 0.01 N HCl, and the combined organic layers were dried over sodium sulfate. After removal of the solvent the residue was purified by column chromatography (silica 60) yielding 573 mg (68%) of 3-(N,N-dimethylammoniumethylenediamine-N'-carbamoyl)-estrone-hydrochloride X as a colorless solid.

Scheme I
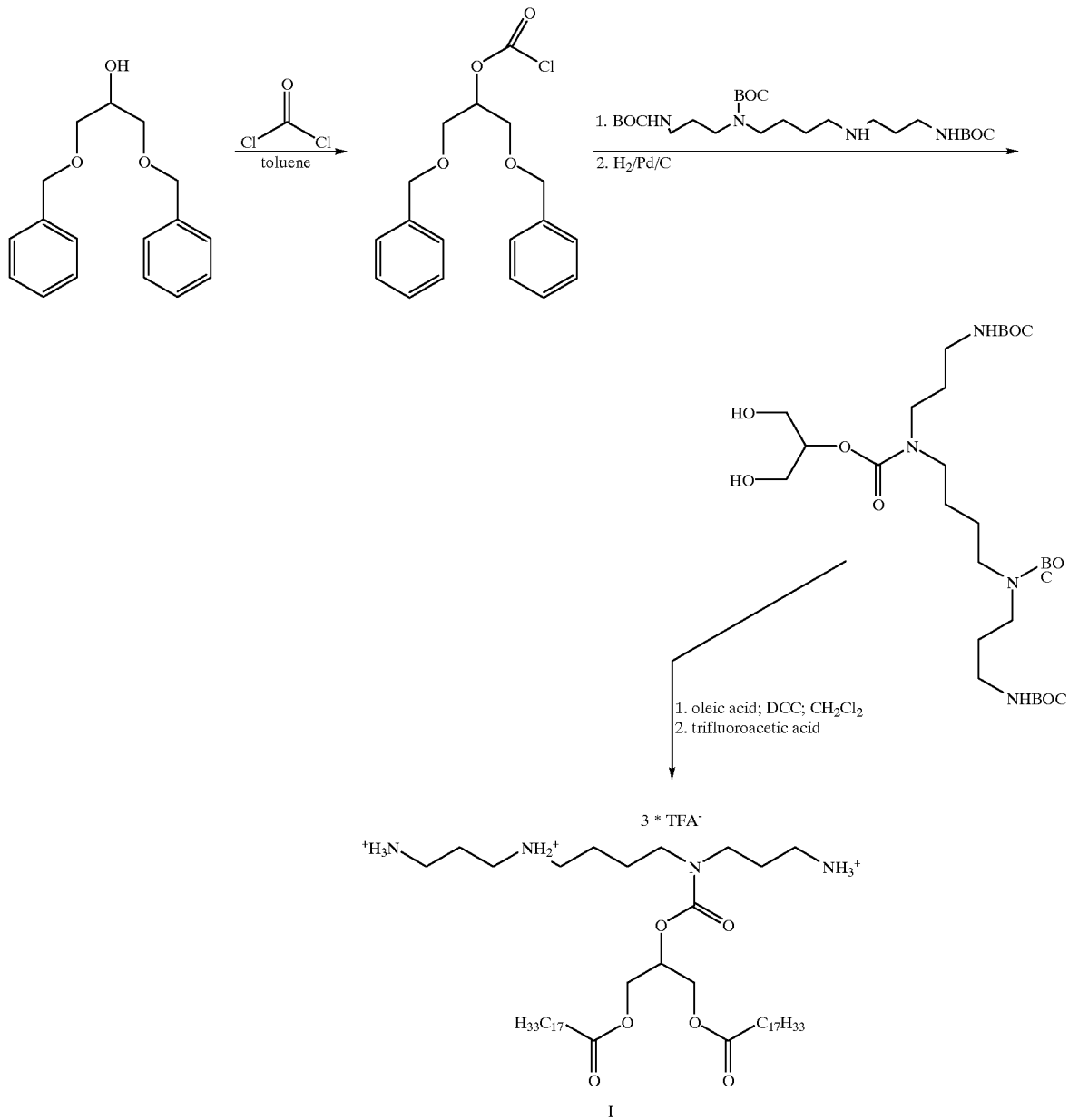

Scheme II
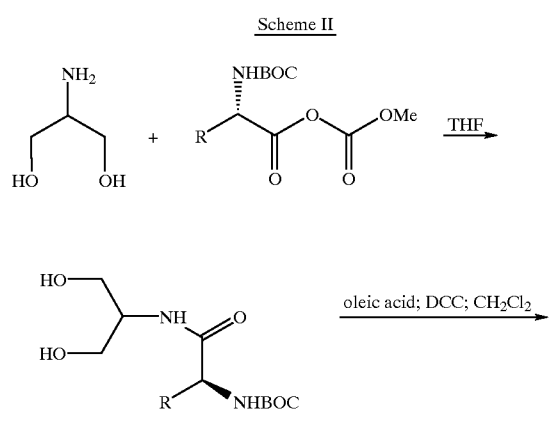
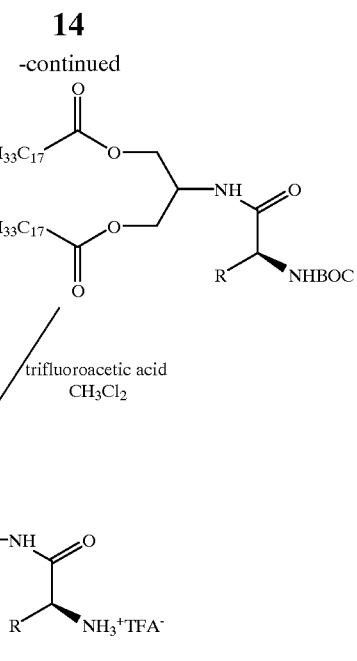
Scheme III
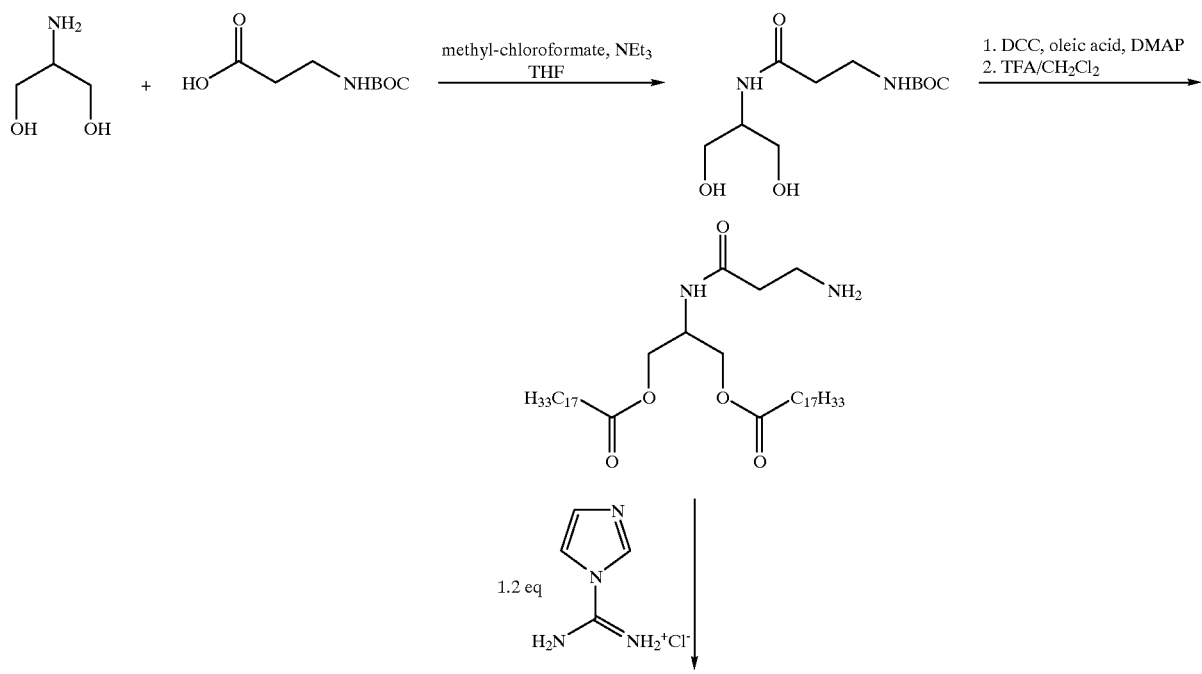

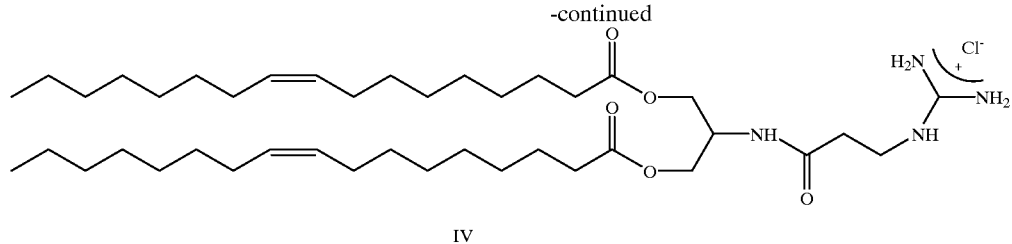
IV
Scheme IV
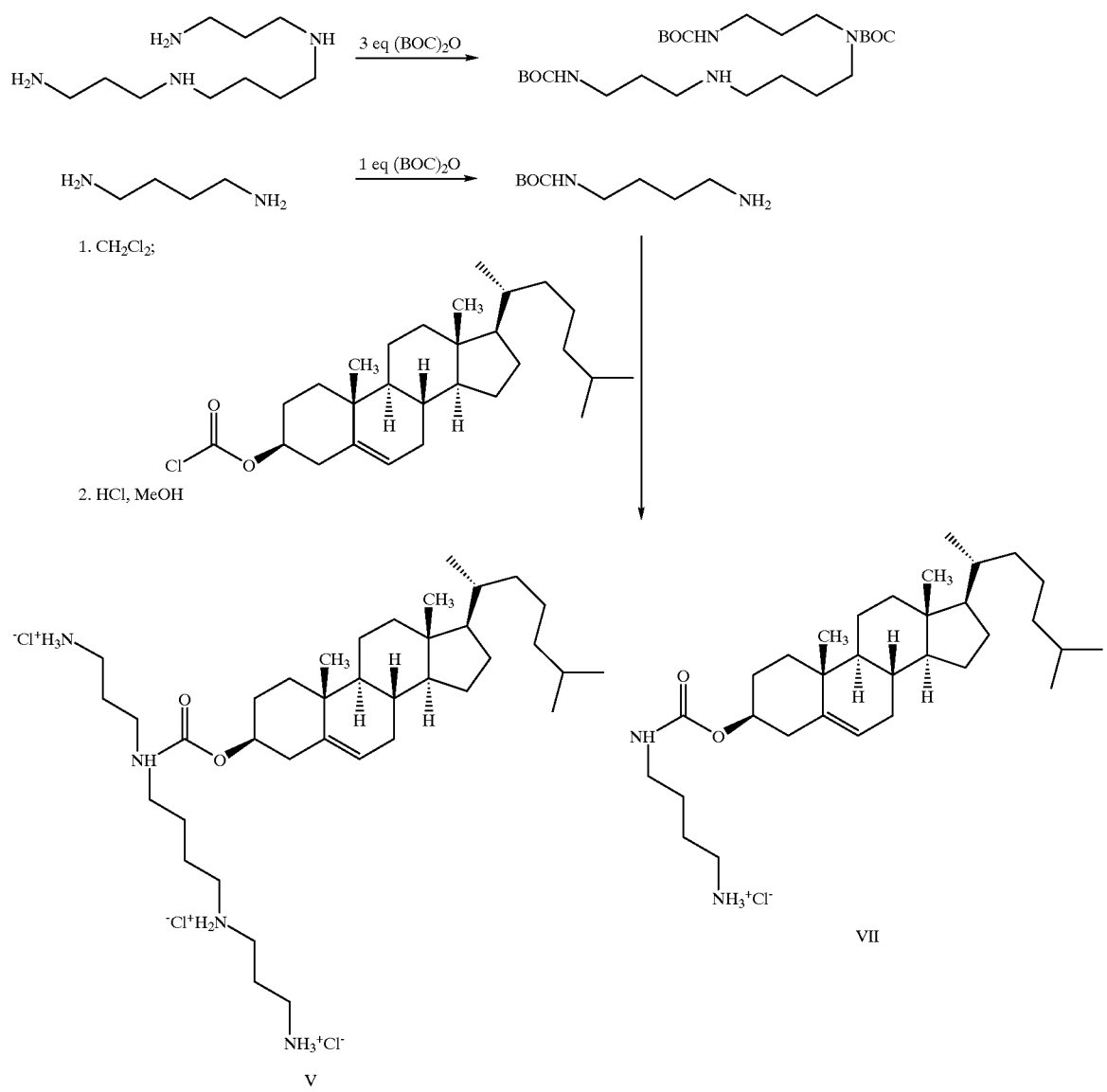

Scheme V
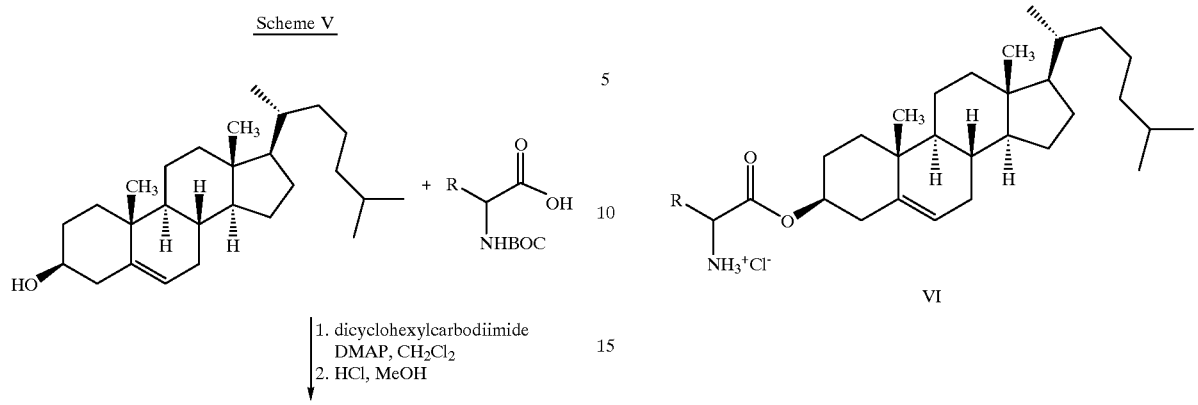
Scheme VI
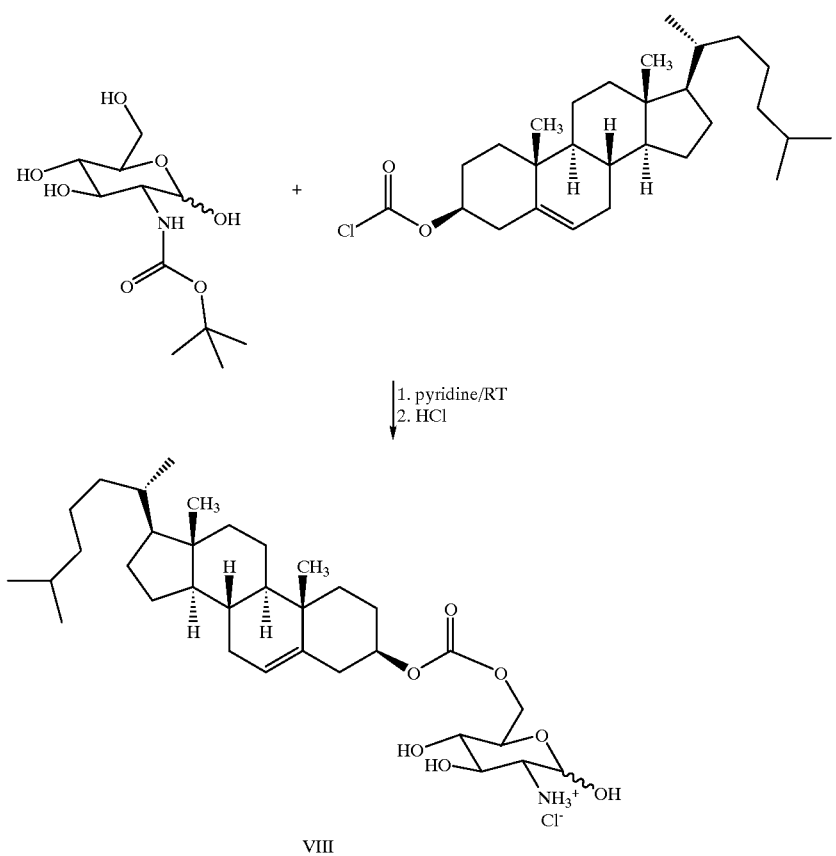

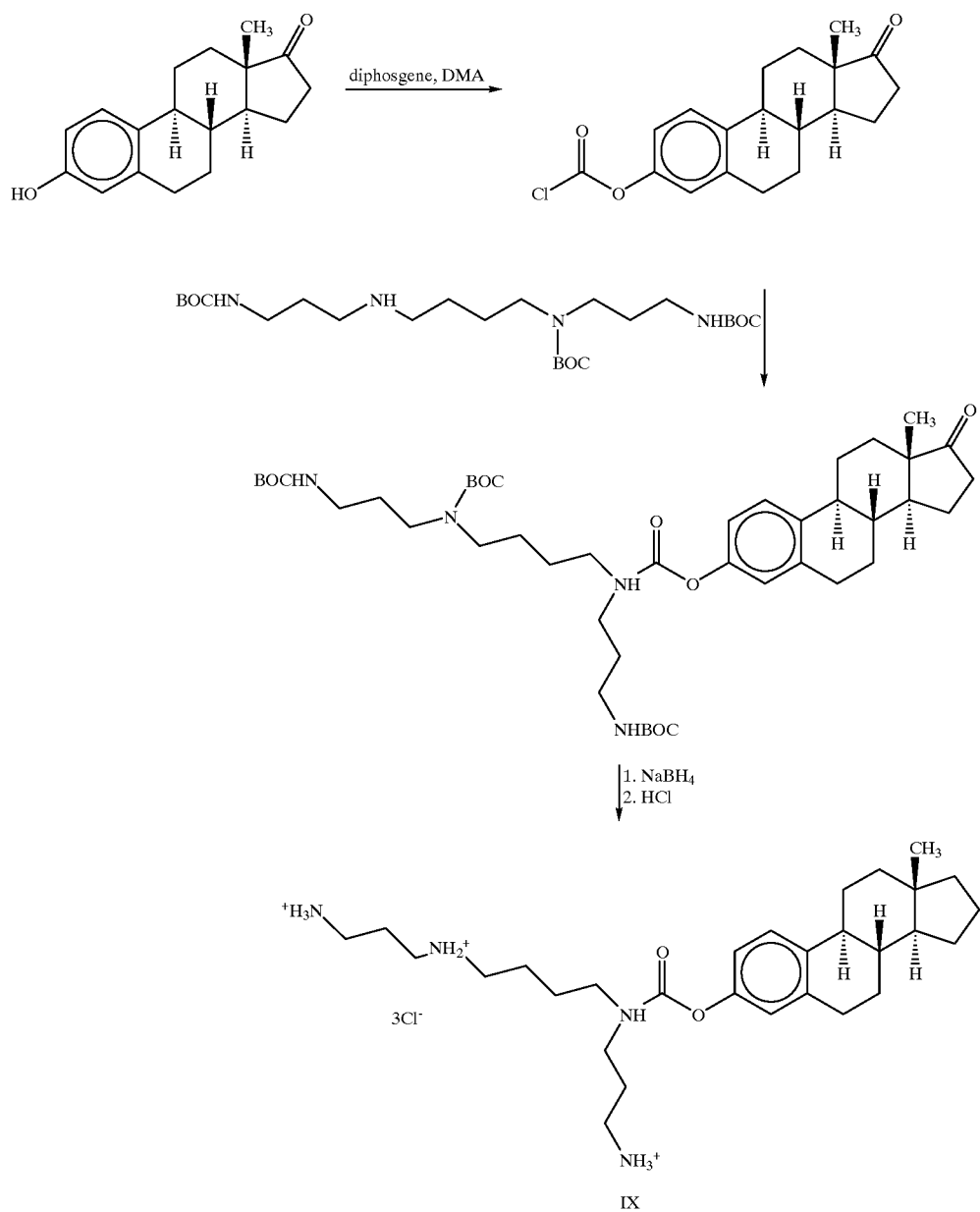
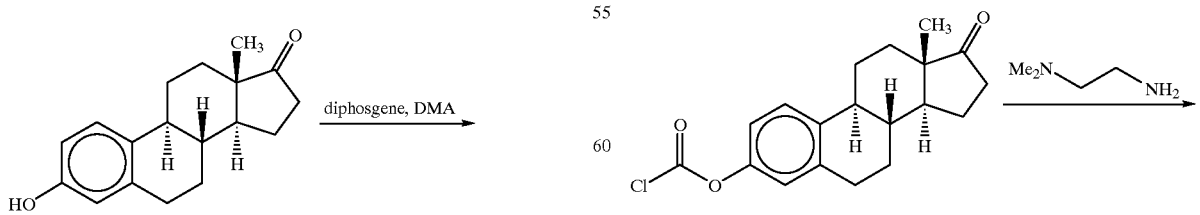

-continued

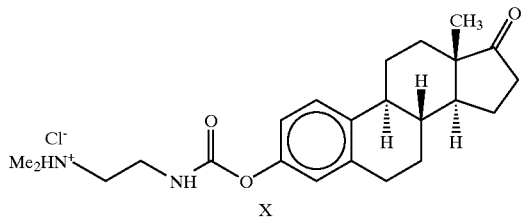

What is claimed is:

1. Cationic lipids for liposomal gene transfer comprising a general formula Ia,

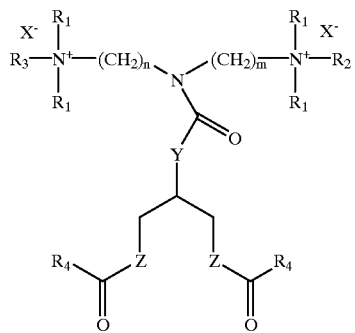

wherein n=2, 3, 4, 6, or 8 and m=2, 3, 6, or 8 and $R_1$=H, $CH_3$, or $CH_2CH_2OH$; $R_2$=H, $CH_3$, $CH_2CH_2OH$, or $(CH_2)_3N^+(R_1)_3$, $R_3$=H, $CH_3$, $CH_2CH_2OH$, or $(CH_2)_3N^+(R_1)_3$, $R_4$ represents a straight chain saturated or unsaturated aliphatic group $C_7$–$C_{21}$, Z=$CH_2$, O, or NH, Y=$CH_2$, O or NH and X=Cl, Br, I, $CH_3COO$, or $CF_3COO$.

2. The cationic lipids of claim 1, wherein when Z=O, Y is not NH.

3. The cationic lipids of claim 1, wherein the formula is

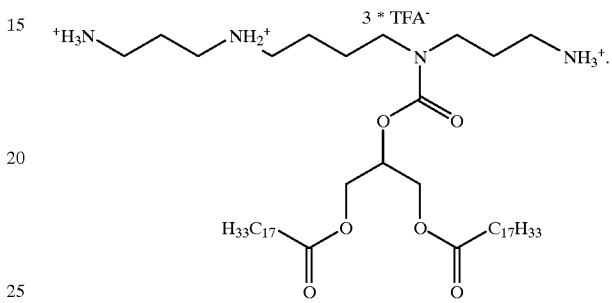

* * * * *